United States Patent [19]

Miller

[11] Patent Number: 5,556,787
[45] Date of Patent: Sep. 17, 1996

[54] MANGANESE III METHOD FOR CHEMICAL OXYGEN DEMAND ANALYSIS

[75] Inventor: Donald G. Miller, Slater, Iowa

[73] Assignee: Hach Company, Ames, Iowa

[21] Appl. No.: 475,187

[22] Filed: Jun. 7, 1995

[51] Int. Cl.$^6$ ................................... G01N 33/18
[52] U.S. Cl. ............. 436/62; 436/164; 436/166; 422/61; 422/79
[58] Field of Search .............. 422/79, 61; 436/62, 436/164, 166

[56] References Cited

U.S. PATENT DOCUMENTS

| | | | |
|---|---|---|---|
| 2,462,050 | 2/1949 | Zimmerman | 562/46 |
| 3,540,845 | 11/1970 | Overbeck et al. | 436/62 |
| 3,558,277 | 1/1971 | Laman et al. | 23/230 |
| 4,394,184 | 7/1983 | Adams | 148/6.15 R |
| 4,430,243 | 2/1984 | Bragg | 252/91 |
| 4,728,455 | 3/1988 | Rerek | 252/99 |
| 4,749,552 | 6/1988 | Sakisako et al. | 422/75 |
| 4,942,133 | 7/1990 | Pauly et al. | 436/125 |
| 5,001,070 | 3/1991 | Ivaska et al. | 436/133 |
| 5,114,606 | 5/1992 | Van Vliet et al. | 252/103 |
| 5,246,621 | 9/1993 | Favre et al. | 252/186.33 |

FOREIGN PATENT DOCUMENTS

| | | | |
|---|---|---|---|
| 20540 | 1/1993 | Australia | 436/62 |
| 56-118668 | 9/1981 | Japan | 436/62 |
| 63-186147A | 8/1988 | Japan . | |
| 139771 | 1/1960 | U.S.S.R. | 436/62 |

OTHER PUBLICATIONS

Barek, et al., Chemia Analityczna,20,749(1975).
Suwyn, et al., Inorganic Chemistry, vol.6, No.1, Jan. 1967.
Stone, et al., Environ. Sci. Technol., 18,450–456 (1984).
Selim, et al., Anal. Chim. Acta, vol. 21 (1959), 536–544.
Gibbs, "Introduction to Chemical Oxygen Demand, Technical Information Series–Booklett No. 8", Hach Technical Center, copyright 1979, 1985, 1990, 1992, 1993.
Hach Water Analysis Handbook, 2nd Edition, pp. 475–506 (1992).
Gorbachev, et al., "Production of Trivalent Managanese", Zhurnal Obshchei Khimii, vol. 10, No. 22, pp. 1961–1967 (1940).
Sem, "Electrooxidation of Managanous Salts and Some Compounds Obtained Thereby" Zeitschrift Für Electrochemie, vol. 21, No. 17/18, pp. 426–437 (1915).
Brochure–Hach Cod System for Wastewater Testing, copyright 1990, 1992, 1993, Bulletin No. 4187.
A. R. J. P. Ubbelohde *J. Chem. Soc.* 1935, 1605–1607.
R. Belcher et al. *Anal. Chim. Acta.* 1952, 6, 322–332.
W. A. Waters *Quart. Rev* 1958, 277–300.
M. Ajmal et al. *Chem. Abstr.* 1964, 60, 3e.
T. J. Kemp et al. *J. Chem. Soc.* 1964, 339–347.
N. Hlasivcova et al. *Collect, Czech. Chem. Commun.* 1969, 34, 3995–4000.
A. M. Jirlca et al. *Anal. Chem.*1975, 47, 1397–1402.
M. S. Nasr et al. *Chem Abstr*, 1975, 83, 102 855p.
J. Barek et al. *Collect. Czech. Chem. Commun,* 1978, 43, 2555–2564.
R. R. Himebaugh et al. *Anal. Chem.* 1979, 51, 1085–1087.
A. T. Kuhn et al *J. Chem. Soc., Faraday Trans. 1* 1983, 79, 417–430.
M. S. Ramachandran et al. *Chem. Abstr.* 1984, 101, 98486g.
R. C. Schothorst et al. *Anal. Chim. Acta.* 1986, 179, 299–305.
M. A. Malati et al. *Analyst* 1987, 112, 511–513.
I. Pinto et al. *Analyst.* 1991, 116, 285–289.

*Primary Examiner*—Arlen Soderquist
*Attorney, Agent, or Firm*—Zarley, McKee, Thomte, Voorhees, & Sease

[57] ABSTRACT

A method of analyzing aqueous samples for Chemical Oxygen Demand (COD) which involves using an analysis reagent comprised of a mixture of stabilized Manganese III ion and an inorganic non-oxidizing acid such as sulfuric or phosphoric acid. Manganese III ion (or manganosulfuric acid complex) is purple, and, as it is reduced to Manganese II ion, the purple color decreases to colorless. Manganese III Chemical Oxygen Demand test is preferred over the presently available chromium reagent test because Chromium VI ion is a known carcinogen, the reagent is photosensitive and a silver catalyst is required. Manganese III is not carcinogenic or photosensitive and does not require a silver catalyst.

21 Claims, No Drawings

MANGANESE III METHOD FOR CHEMICAL OXYGEN DEMAND ANALYSIS

FIELD OF THE INVENTION

The field of the present invention relates to tests for determination of Chemical Oxygen Demand in aqueous samples.

BACKGROUND OF THE INVENTION

Oxygen demand is an important parameter for determining the effect of organic pollutants on receiving water. As microorganisms in the environment consume these materials, oxygen is depleted from the water. This can have an adverse effect on fish and plant life.

There are three main methods of measuring oxygen demand: directly, by biochemical oxygen demand (BOD) and/or chemical oxygen demand (COD), and indirectly by total organic carbon (TOC) procedures. BOD, because it uses microorganisms for oxidation, gives the closest picture of the biological processes occurring in a stream. However, results are not available for five days, and the BOD test is inadequate as an indicator of organic pollution when used with industrial wastewater containing toxic materials which poison the microorganisms and render them unable to oxidize wastes.

Unlike BOD, the two other methods do not use biological processes and are therefore faster. A strong oxidizing agent or combustion technique is used under controlled conditions in the TOC method to measure the total amount of organic material in a sample. The results obtained may not be as accurate as the results reached through the COD or BOD method in predicting environmental oxygen demand because oxygen demands may differ between compounds with the same number of organic carbons in their structures. The difference in oxygen demand between two compounds containing the same amount of organic carbon can be seen in the following equations showing the oxidation of oxalic acid and ethanol:

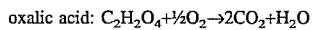

oxalic acid: $C_2H_2O_4 + \frac{1}{2}O_2 \rightarrow 2CO_2 + H_2O$

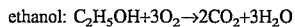

ethanol: $C_2H_5OH + 3O_2 \rightarrow 2CO_2 + 3H_2O$

Each molecule of ethanol uses up six times as much oxygen as an equivalent amount of oxalic acid and thus would have a much greater effect on the dissolved oxygen present in a receiving water. Estimating environmental oxygen demand (as with BOD and COD) requires complete oxidation of carbon and hydrogen present in the organic matter. Thus, while TOC is a more direct expression of total organic content than BOD or COD, it does not provide the same kind of information. An empirical relationship can exist between TOC, BOD and COD, but the specific relationship must be established for a specific set of sample conditions.

Currently, the COD test has a fairly specific and universal meaning: the oxygen equivalent of the amount of organic matter oxidizable by potassium dichromate in a 50% sulfuric acid solution. Generally, a silver compound is added as a catalyst to promote the oxidation of certain classes of organics. A mercuric (or other) compound may also be added to reduce interference from the oxidation of chloride ions by the dichromate which will give false high COD readings. The end products of organic oxidations are carbon dioxide and water.

After the oxidation step is completed, the amount of dichromate consumed is determined either titrimetrically or colorimetrically. Either the amount of dichromate reduced (Chromium III) or the amount of unreacted dichromate (Chromium VI) remaining can be measured. If the latter method and colorimetry are chosen, the analyst must know the precise amount of dichromate added and be able to set the instrument wavelength very accurately since readings are routinely taken on the "shoulder" of the Chromium VI absorbance peak. Wavelength settings must be reproduced precisely in order to avoid errors when using a previously generated calibration curve.

Dichromate was first used in the COD test over 50 years ago. Before that time, potassium permanganate was the oxidant of choice. Analysts have tried many other reagents such as potassium persulfate, cerium sulfate, potassium iodate and oxygen itself. Generally these other oxidants have not been satisfactory.

While oxidation of organic materials by dichromate in sulfuric acid has been the method of choice for perhaps 50 years, it too is not without limitations. However, through careful research, many COD method limitations have been overcome or significantly reduced. For example, incomplete oxidation of aliphatic hydrocarbons, organic acids and alcohols has been improved by using silver ions as a catalyst, although heterocyclic compounds containing nitrogen still present difficulties. Interference from oxidation of chloride can be reduced by the addition of mercuric (or other) ions to the sample. A simple mathematic correction is not sufficient because chloride is not always oxidized quantitatively. In addition, the presence of chloride enhances the interference of ammonia nitrogen. Mercuric (or other) ions form a soluble complex with chloride which largely eliminates its interference up to 2000 mg/L. An alternative method for sea water and brines is to collect chlorine produced by oxidation in a potassium iodide solution and titrate to determine the correction factor. The addition of mercury is undesirable from a pollution standpoint; however, when mercury is used, it is required by law to be recovered and recycled.

Although nitrite is seldom present at high enough levels to cause significant interference, it can be eliminated by adding sulfamic acid. If high concentrations of other reducing or oxidizing agents are present, a separate analysis and correction may be necessary in all methods.

The relatively long two-hour digestion time now in use can be reduced if caution is observed. Many types of wastes are digested completely in 30 minutes or less at 150° C., the normal operating temperature. The time of complete digestion can be recognized by an experienced operator or (more efficiently) by using a colorimetric reading with the micro method explained subsequently. In this approach, many consecutive readings taken on a single sample are used to determine when there is no further change in dichromate concentration due to reduction. At this point, the oxidation would be considered complete and the final determination could be performed. The escape of volatile organics, cumbersome equipment and large amounts of expensive silver compounds called for in the EPA and Standard Methods Open Reflux procedures have all been eliminated by the micro method. Sealed digestion containers prevent the escape of volatiles and eliminate the need for condensers. When the water sample is added to the acid dichromate solution, it forms a layer on top due to the difference in density between the water and the acid. When the water and acid mix, the heat generated can drive off some of the volatiles. (Some volatiles are not driven off until higher temperatures are reached during the heating process.) Loss of volatiles is prevented by having the cap screwed onto the vial when the mixing and subsequent heating occurs in the micro method.

The chemistry of COD digestions when using dichromate in sulfuric acid is well known. The carbon compounds are converted to carbon dioxide while hydrogen liberated from hydrocarbons is converted to water. Other elements may also be oxidized. There is some disagreement, however, as to what "complete" oxidation is, especially when nitrogen-containing compounds are present. The main reaction is illustrated in Equation 1 with potassium acid phthalate (KHP) used as an example.

$$2KC_8H_5O_4 + 10K_2Cr_2O_7 + 41H_2SO_4 \rightarrow 16CO_2 + 46H_2O + 10Cr_2(SO_4)_3 + 11K_2SO_4 \quad (1)$$

Because each molecule of $K_2Cr_2O_7$ has the same oxidizing power as 1.5 molecules of $O_2$, the equivalent reaction is:

$$2KC_8H_5O_4 + 15O_2 + H_2SO_4 \rightarrow 16CO_2 + 6H_2O + K_2SO_4 \quad (2)$$

Thus, two (2) molecules of potassium acid phthalate (KHP) consume 15 molecules of oxygen. On a weight basis, the theoretical COD for one (1) milligram (mg) of KHP is 1.175 mg of oxygen.

In spite of the approved technology of dichromate in sulfuric acid testing as above described, there remain several problems with the dichromate COD test. In the first instance, Chromium VI (dichromate) is a known carcinogen, and therefore those making up the samples are exposed to a potential risk from Chromium VI. Secondly, when Chromium VI is reduced to Chromium III there is a color change from a yellowish-orange to green. Thus, the dichromate analysis includes a two-color system that does not lend itself to visual analysis and can require very accurate instrumental wavelength settings. Third, the dichromate reagent is photosensitive, and the results can be affected by prolonged exposure to light. Fourth, to properly do the analysis, as earlier mentioned, silver ion is needed as a catalyst and mercuric (or other) ion is needed to effect the removal of chloride. Obviously, since one is measuring the amount of organic material in the aqueous sample, any dichromate used in oxidation of inorganics such as chloride causes an error in the COD analysis results. Thus mercuric (or other) ion is commonly added to rid the system of chloride interference. Silver is expensive and heavy metals such as silver and mercury need to be reclaimed and recycled due to possible environmental problems.

It can therefore be seen that there is a continuing need for the development of new and accurate COD tests. This invention has as its primary objective the fulfillment of the need for the development of a new test which does not employ a dichromate in sulfuric acid analysis.

Another objective of the present invention is to provide a COD test which is based upon a non-photosensitive, non-carcinogenic, stable oxidizing agent.

A further objective of the present invention is to provide a Manganese III ion based COD test system.

An even further objective of the present invention is to provide a system which employs a single color change, making the test results easy to read visually using a color comparator device or instrumentally using a colorimeter or spectrophotometer on either an intermittent or continuous basis.

Still another objective of the present invention is to prepare a COD test system which is inexpensive to produce and easy to make while minimizing the risks involved in handling potentially hazardous chemicals.

The method and means of accomplishing each of the above objectives as well as others will become apparent from the detailed description of the invention which follows hereinafter.

SUMMARY OF THE INVENTION

Chemical oxygen demand determinations of aqueous samples are made involving a reagent which does not use dichromate in sulfuric acid. Instead, the basis for the reagent is stabilized Manganese III ion which may be used in inorganic acids such as sulfuric acid. Stabilized Manganese III ion in the new test method is reduced to Manganese II ion by organic matter with the intensity of the purple color from the Manganese III ion becoming less as Manganese III ion is reduced to colorless Manganese II ion. The test results can be determined by measuring the amount of this single color change visually, using a color comparator device, or, instrumentally, using a colorimeter or spectrophotometer. It can also be determined by titration using a standardized reducing solution and an indicator to sharpen the titration endpoint. Test results correlate well to results obtained from conventional dichromate in sulfuric acid COD tests. It does not have the disadvantage of using carcinogens, multiple colors, expensive silver catalyst, or of being photosensitive as do dichromate in sulfuric acid COD tests.

DETAILED DESCRIPTION OF THE INVENTION

The process of the present invention uses COD measurements and reagent testing procedures commonly used with dichromate and sulfuric acid analysis but practiced using a greatly different reagent system. In the present system the reagent basis is Manganese III ion as the oxidizing agent.

Considering all of the oxidizing agents that have been theorized, proposed and/or used in the past for COD analysis, it is somewhat surprising that Manganese III ion has been essentially overlooked. By way of example, even Dr. Linus Pauling in his *General Chemistry* text has described the Manganese III ion as a strong oxidizing agent, but indicates that its salts are unimportant (Pauling, *General Chemistry*, W. H. Freeman and Company, 1948).

It is generally believed that Manganese III ion has not been regarded as a candidate for COD testing for three reasons. First, it is virtually insoluble in water or concentrated sulfuric acid. It is known to be partially soluble in dilute sulfuric acid with maximum solubility occurring at about 10 to 12 Normal acid concentration and decreasing at a moderate rate in both directions (i.e., increasing and decreasing acid normalities) except for another slight increase in solubility in the region of 21 to 27 Normal acid concentration that was discovered. It was also discovered that Manganese III has a tendency to form supersaturated solutions. When precipitation of Manganese III compounds then occurs later in time, the precipitate looks visually very much like the more common Manganese (IV) Dioxide, which would could lead to the mistaken conclusion that decomposition had occurred. Second, the Manganese III ion does undergo disproportionation or auto-oxidation/reduction reactions, forming Manganese II and Manganese IV ions and/or salts, depending on the combination of several factors including time, temperature, acid concentration, Manganese III concentration, sample size and the introduction of stabilizing ions or complexes. By adjusting these factors it was possible to prepare a stable formulation with an acid normality in the region of 14 to 20 Normal which was also stable on dilution with the aqueous sample to 12 to 18 Normal acid on digestion at 100 to 160 degrees C for up to four (4) hours and containing sufficient Manganese III ion to accommodate up to 1100 mg/L COD for the Standard Range test and 2750 mg/L for the High Range test. These are the preferred and optimum acid concentration ranges and time/ temperature conditions for the present invention though other stable combinations are possible. Third, the use of other ions and complexers to stabilize Manganese III ion in solution (such as sulfate, phosphate, Manganese II ion, etc.) have been reported in the literature but may not be widely known.

While the oxidizing agent for the present invention is Manganese III ion, the acid may be sulfuric, phosphoric, or any other inorganic acid of sufficient concentration or stability to accommodate the reaction conditions, or any combination or mixtures thereof. Since sulfuric acid is virtually ubiquitous and least expensive, no advantage is seen for phosphoric or other acids, though they can be used.

Manganese III ion must be stabilized in the Manganese III state. It is stabilized in two ways in this reagent. First, the use of sulfuric or phosphoric acids results in the formation of stable, soluble, manganosulfuric or manganophosphoric Manganese III complexes, respectively. Second, since Manganese III is known to disproportionate to Manganese IV and Manganese II in an auto-oxidation reduction reaction, this reaction can be preferentially shifted to stabilize Manganese III through use of the Law of Mass Action (also known as Le Chatelier's Principle) whereby the reaction equilibrium is shifted by increasing the concentration of one of the components. Simply introducing more Manganese II ion into the reagent (usually added as, but not limited to, Manganese II Sulfate) causes the disproportionation reaction to be much less likely to occur, hence, stabilizing the Manganese III ion.

Preferably the Manganese III ion is stabilized by Manganese II ion with the ratio of Manganese II ion to Manganese III ion being from about 0.5:1 molar ratio to about 5.0:1 molar ratio. A preferred molar ratio range is from about 2.0:1 to about 4.0:1. The most preferred range is from about 3.0:1 to about 3.5:1 of MnII:MnIII. Again, solubility plays an important role in determining the final matrix with the Manganese II ion solubility decreasing as acid concentration increases.

As earlier stated, the concentration of the sulfuric acid or other inorganic acid present must be in a concentration sufficient to stabilize the manganese reagent, and as well, to assist in the oxidation of the organics in the aqueous sample. The ranges of normality earlier expressed are those suited for the reagent system of the present invention.

If desired, the aqueous sample can be pretreated to remove interfering chloride ions. If mercuric ions are added for "in situ" chloride removal via complexation as previously described, the test solution must be reprocessed to recover the mercury and recycle it. In this way, mercury release to the environment can be avoided. Since the Manganese III test system uses a smaller aqueous sample, it requires only ¼ of the amount of mercury per test as does the dichromate/sulfuric micro method. The Manganese III test system works well with either chloride removal pretreatment or in situ mercuric ion chloride removal systems in the analysis of aqueous samples.

Manganese III ion (free or in complexes) is purple in color. As it is reduced to Manganese II ion (free or complexed) it changes to colorless. Thus, the COD can be measured in one of three ways. First, it can be determined by comparing the Manganese III color in the digested solution visually to a colored standard of known concentration. Second, the intensity of the Manganese III color can be determined instrumentally using a colorimeter or spectrophotometer by measuring changes in either absorbance or transmittence with results determined on a precalibrated scale or graph. Third, the digested solution can be titrated using a standardized reducing agent (such as ferrous ammonium sulfate) in solution. An indicator (such as ferroin) is typically used to produce a sharp titration endpoint. The micro method in conjunction with instrumental reading of results is the most widely used combination. The micro method is preferred due to the aforementioned higher recovery of volatile organics and the minimization of reagents needed for the test, hence, a lower cost. The instrumental readings are preferred because they are fast and accurate even though the instruments do have a significant initial cost. The simplest, lowest cost method is the visual method which provides reasonable results (though less precise than instrumental or titration results) when used with a color comparator device and standard that is accurate in hue and intensity reproduction of the Manganese III purple color. The least desirable and least practiced method is titration. It requires a reducing titration solution that may need to be repeatedly re-standardized at regular intervals as it ages. The procedure also calls for a judgment by the analyst as to when the endpoint has been reached in addition to having to calculate the COD concentration from titration data.

The amount of reagent employed in the test will vary depending upon the estimated COD of the sample. For example, COD tests (with results measured as milligrams per liter of oxygen) use different amounts of reagents, depending upon whether the COD value falls within the standard range (20 to 1000) or the high range (50 to 2500 mg/L COD). Nevertheless, the ratios herein expressed of reagent concentrations remain unchanged with the amount of volume of reagent simply varied. The volume of reagent for the standard range is 6.25 mL per test and for the high range is 6.55 mL per test, each giving a total volume of 6.75 mL per test when 0.5 and 0.2 mL samples are added, respectively.

Typically the reagent is supplied in a sample vial made of but not limited to glass, with a removable closure or seal (usually a cap) that is inert to sulfuric and/or other inorganic acids and to the Manganese III oxidant. A Teflon or other inert seal is used in the cap liner to contain the reagent without contaminating it. In ordinary use, the cap of the vial is unscrewed and the sample is added to the vial (0.5 mL for the standard range and 0.2 mL for the high range) containing the Manganese III/Manganese II/sulfuric acid reagent. The vial is then recapped and the solution mixed by inverting the vial repeatedly. The vial is then heated at 100° C. to 160° C., preferably 150° C. for one hour (up to two hours for more difficult organics, or, less than one hour for easier to digest organics as determined by the operator on similar samples. Different calibrations may be required for different heating periods. During the heating step, the organic material in the sample is oxidized and the Manganese III is quantitatively reduced to Manganese II. After digestion, the vial is cooled to room temperature, first in air for two (2) minutes, then in flowing tap water or a water bath for three (3) to five (5) minutes, or until room temperature is reached. A visual, instrumental (usually at 510 nm) or titrimetric determination of COD is then made.

If the titrimetric determination is the method of choice, generally the digested solutions are titrated with Ferrous Ammonium Sulfate Standard Solution, 0.0625 Normal, using Ferroin Indicator to produce a vivid color change at the endpoint. The sequence of observed color changes during the titration is purple to light green or colorless (depending on the strength of the Ferroin Indicator) to a sharp change to orange or orange-brown at the endpoint.

Since Biological Oxygen Demand (BOD) is the standard test method for determining oxygen demand in waters and wastewaters, the accuracy of COD analyses is normally based on how well it correlates to BOD. Since the dichromate/sulfuric acid COD system has been used for many years and is known to correlate well to BOD results, comparisons of analyses using the same samples with the proposed Manganese III/Sulfuric Acid system and the dichromate/sulfuric acid system should provide an accurate estimate of the correlation of Manganese III/Sulfuric Acid reagent results with expected BOD values.

The following examples are offered to illustrate, but not limit the process of the present invention.

EXAMPLES

Wastewater samples were gathered from various Standard Industrial Classification (SIC) sources expected to represent, but not be limited to, those real-world samples currently being tested for COD. They are also expected to contain organic compounds ranging from easy to difficult to oxidize. Samples were analyzed by both the aforedescribed Manganese III method (adding mercuric ion to remove chloride interference) and the EPA-Approved Chromium VI Closed Reflux method containing mercury and silver ions. Two-hour digestions at 150° C. in identical containers were performed for both methods with results measured by spectrophotometric readings. Values are all expressed as mg/L COD and were taken from calibration curves generated for both methods using the test procedures previously described and Potassium Acid Phthalate (KHP) COD standards of known values. The results are given in Table I.

TABLE I

WASTEWATER SAMPLE DATA

| Sample | SIC No. | Mn((III)COD | Cr(VI)COD | Mn/Cr Ratio % |
|---|---|---|---|---|
| 1 | 2819 | 1976 | 2140 | 92.3 |
| 2 | 2819 | 2125 | 2325 | 91.4 |
| 3 | 2819 | 10130 | 11540 | 87.8 |
| 4 | 2819 | 2715 | 3070 | 88.4 |
| 5 | 2819 | 10400 | 11760 | 88.4 |
| 6 | 2819 | 2000 | 2150 | 93.0 |
| 7 | 2821 | 1988 | 2188 | 90.9 |
| 8 | 2821 | 250 | 273 | 91.6 |
| 9 | 2821 | 2280 | 2160 | 106 |
| 10 | 2869 | 354 | 388 | 91.2 |
| 11 | 2869 | 50 | 56 | 89.3 |
| 12 | 2869 | 2380 | 2970 | 80.1 |
| 13 | 2911 | 120 | 111 | 108 |
| 14 | 2911 | 28 | 32 | 87.5 |
| 15 | 2911 | 127 | 132 | 96.2 |
| 16 | 2911 | 31 | 33 | 93.9 |
| 17 | 2911 | 146 | 149 | 98.0 |
| 18 | 2911 | 108 | 107 | 101 |
| 19 | 4952 | 684 | 718 | 95.3 |
| 20 | 4952 | 38 | 40 | 95.0 |
| 21 | 4952 | 228 | 248 | 91.9 |
| 22 | 4952 | 36 | 43 | 83.7 |
| 23 | 4952 | 100 | 101 | 99.0 |
| 24 | 4952 | 86 | 85 | 101 |

The average percentage COD recovery for the Manganese III method for all samples tested is 89.6, or, about 90% of the average values obtained for the Chromium VI method. Variation is within +/− 10% of the Manganese III method average for all but four samples at 16, 18, 11 and 11%, respectively, for samples 9, 13, 18 and 24. All sample values fall easily within +/− 20% of the Manganese III method average compared to the standard Chromium VI method. It is easily seen that running both methods on a given sample or class of samples to generate a correlation (or calibration) factor between methods allows Manganese III test values to provide a highly accurate estimate of Chromium VI COD values. It can be seen that the test results are closely parallel to and fall within the stated accuracy of the dichromate-system data. It can therefore be seen that the invention accomplishes at least all of its stated objectives.

What is claimed is:

1. A method of analysis of aqueous samples for Chemical Oxygen Demand (COD), said method comprising:

using as an analysis reagent a mixture of stabilized Mn III ion and a concentrated inorganic acid, and adding to said analysis reagent a test amount of an aqueous sample, and thereafter determining from the amount of Mn III ion reduced to Mn II ion, the COD of said aqueous sample.

2. The method of claim 1 wherein the Mn III ion is stabilized in Mn III state by addition of Mn II ion.

3. The method of claim 2 wherein the molar ratio of Mn II ion to Mn III ion is from about 0.5:1 to about 5.0:1.

4. The method of claim 3 wherein the molar ratio of Mn II ion to Mn III ion is from about 2.0:1 to about 4.0:1.

5. The method of claim 5 wherein the molar ratio of Mn II ion to Mn III ion is from about 3.0:1 to about 3.5:1.

6. The method of claim 1 wherein the inorganic acid is selected from the group consisting of sulfuric acid, phosphoric acid or other non-oxidizing inorganic acids, and mixtures thereof.

7. The method of claim 6 wherein the acid is sulfuric acid.

8. The method of claim 7 wherein the sulfuric acid is sufficiently concentrated to assist in stabilizing the analysis reagent and to assist in the oxidation of the aqueous sample.

9. The method of claim 7 wherein the sulfuric acid is from about 14N to about 20N.

10. The method of claim 9 wherein the sulfuric acid is from about 16N to about 18N.

11. The method of claim 1 wherein the aqueous sample is pretreated to remove interfering chloride ions.

12. The method of claim 1 wherein the analysis reagent contains an added ion in an amount sufficient to remove interfering chloride.

13. The process of claims 1 wherein determining the COD of said aqueous sample is a colorimetric or spectrophotometric determination based upon the intensity of the Mn III ion color in the oxidized sample/analysis reagent mixture.

14. The process of claim 2 wherein determining of the COD of said aqueous sample is a titrimetric determination.

15. The process of claim 1 wherein determining of the COD of said aqueous sample is a visual determination using a color standard and a color comparator.

16. A method of analysis of aqueous samples for Chemical Oxygen Demand (COD), said method comprising:

using as an analysis reagent a mixture of stabilized Mn III ion and concentrated sulfuric acid;

adding to the analysis reagent an aqueous test sample in an amount sufficient for COD determination;

heating the test sample to a temperature between 100° C. and 200° C.; and holding the test sample at said temperature for an amount of time sufficient to oxidize organic materials present in said test sample;

cooling said test sample; and thereafter determining from the amount of Mn III ion reduced to Mn II ion, the COD of said aqueous sample.

17. The method of claim 16 wherein the heating temperature is from about 140° C. to about 160° C.

18. A closed vessel reagent system for testing COD of aqueous samples, comprising:

a tube for holding analysis reagent;

said tube having a removable but acid inert covering cap;

said tube containing sulfuric acid having a concentration within the range of from about 16N to about 18N; and stabilized Mn III ion.

19. The closed vessel system of claim 18 wherein the Mn III ion is stabilized against disproportionation by adding Mn II ion.

20. The closed vessel system of claim 18 wherein the inert covering cap is a Teflon sealed removable cap.

21. The closed vessel system of claim 18 wherein said system further comprises an additional ion in an amount sufficient to prevent chloride interference with COD measurements.

* * * * *